United States Patent
Duckett et al.

(12)

(10) Patent No.: US 6,340,480 B1
(45) Date of Patent: *Jan. 22, 2002

(54) NATURAL COMPOSITION FOR THE TREATMENT OF CIRCULATORY CONDITIONS

(76) Inventors: Melvin J. Duckett, 10300 Cedar Grave Rd., Sparks, MD (US) 21152; Kyle Moore, 4705 Creekside Cir., Apt. 13, Owings Mills, MD (US) 21117

( * ) Notice: Subject to any disclaimer, the term of this patent is extended or adjusted under 35 U.S.C. 154(b) by 0 days.

This patent is subject to a terminal disclaimer.

(21) Appl. No.: 09/473,105

(22) Filed: Dec. 28, 1999

Related U.S. Application Data

(63) Continuation-in-part of application No. 09/255,587, filed on Feb. 22, 1999, now Pat. No. 6,007,824.
(60) Provisional application No. 60/092,143, filed on Jul. 9, 1998.
(51) Int. Cl.$^7$ ................................................. A61K 35/78
(52) U.S. Cl. ...................... 424/728; 424/727; 424/752; 424/777; 514/565; 514/887; 514/929
(58) Field of Search ............................ 424/195.1, 728, 424/777, 752, 727; 514/565, 887, 929

(56) References Cited

U.S. PATENT DOCUMENTS 5,861,168 A * 1/1999 Cooke et al. ................ 424/424

* cited by examiner

*Primary Examiner*—Christopher R. Tate
(74) *Attorney, Agent, or Firm*—Law Office of Royal W. Craig

(57) ABSTRACT

A composition and method for treating circulatory conditions by promoting systemic vascular relaxation and dilation. Exemplary circulatory conditions are disclosed and include wound healing and/or reduction of hypertension. The composition is a natural combination of L-arginine, ginseng and Zizyphi fructus in an orally or topically administered dosage. The combination works synergistically to synthesize NO and thereby promote systemic vascular relaxation and dilation. The mechanism works in the wound compartment to promote and sustain the wound healing process. Likewise, the combined constituents, when administered orally or topically in proper concentration, work to maintain a critical threshold level of NO in areas that cannot themselves produce it, thereby promoting systemic vascular relaxation and dilation in order to reduce hypertension.

20 Claims, 1 Drawing Sheet ge # NATURAL COMPOSITION FOR THE TREATMENT OF CIRCULATORY CONDITIONS

CROSS-REFERENCE TO RELATED APPLICATIONS

The present application is a continuation-in-part of application Ser. No. 09/255,587 for "NATURAL COMPOSITION AND METHOD FOR THE TREATMENT OF SEXUAL DYSFUNCTION"; filed: Feb. 22, 1999, now U.S. Pat. No. 6,007,824, which is in turn based on provisional application no. 60/092,143, filed Jul. 9, 1998.

BACKGROUND OF THE INVENTION

1. Field of the Invention

The present invention relates to the treatment of circulatory conditions and, more particularly, to an improved natural composition for treatment of an array of conditions by dilation of blood vessels, said conditions including skin wounds, hypertension, etc. The natural composition uses various combinations of L-arginine, ginseng and Zizyphi fructus in a topically or orally administered dosage.

2. Description of the Background

It has been found that an array of conditions can be successfully treated by increasing blood flow to the affected area. The goal of most injury treatments is to accelerate the healing process by increasing the circulation of blood flow to an affected area. This is the recommended treatment for skin wounds, tendonitis, muscular sprains and other injuries to the musculoskeletal system. As a result, there have been a number of studies to determine the most effective compounds and methods for increasing blood flow. There have also been a number of studies to determine the full range of conditions that are amenable to this form of treatment. Many of these studies have cited the vasodilator functions of nitric oxide (NO) as a key factor in the endothelial-mediated microvascular homeostasis that is exhibited in cutaneous tissue.

One example of such a condition plus a useful treatment compound is set forth in co-pending U.S. utility patent application No. 09/255,587 (now issued as U.S. Pat. No. 6,007,824 to the inventors named herein). A composition and method for treating sexual dysfunction was therein disclosed, the natural composition including a combination of L-arginine, ginseng and Zizyphi fructus in an orally administered dosage. The combination acts synergistically to alleviate erectile dysfunction by stimulating enough release of NO in the corpus cavernosum to produce and sustain smooth muscle relaxation, thereby allowing the inflow of blood and alleviating erectile dysfunction. The '587 patent effectively provides a natural medicinal alternative to Viagra® for the treatment of erectile dysfunction.

Further studies have broadened the merits of stimulating NO. Two particular applications include treatment of skin wounds, and treatment of hypertension.

Wound healing is a cooperative process involving platelets, fibroblasts, neutrophils; macrophages, cytokines, growth factors, cellular migration, collagen and matrix deposition, angiogenesis and remodeling. A well-oxygenated vascularized connective tissue compartment is crucial to facilitate the healing process at the wound site.

by 1986, research identified nitric oxide as the endothelium-derived relaxing factor responsible for the maintenance of vascular tone, thus implicating nitric oxide as a potential wound-healing agent. Studies have since confirmed this. See, for example, Schaffer et al., *Acute Protein-calorie Malnutrition Impairs Wound Healing: a Possible Role of Decreased Wound Nitric Oxide Synthesis*, J Am Coll Surg, Jan. 1997 184:1, 37–43.

Nitric oxide regulation of wound repair invokes the following relationships: wound oxygen availability is enhanced by the vasodilator functions of nitric oxide (this is a key factor in the endothelial-mediated microvascular homeostasis that is exhibited in cutaneous tissue); nitric oxide has been demonstrated to be a significant component of the neurogenic vascular response; local random flap survival is dependent upon sustained nitric oxide activity and nitric oxide deficiency has been clinically and experimentally associated with the neuropathic (ischemic) alterations observed in diabetes; the inflammatory mediation of wound repair is enhanced by nitric oxide mediated antimicrobial cytotoxicity and immunomodulation; wound angiogenesis is enhanced through nitric oxide mediated mechanisms; intravascular cellular adhesion (neutrophilendothelial) is inhibited by the action of nitric oxide on the integrins pathway; nitric oxide activity also decreases extravascular free radical cellular peroxidation by integrins inhibition. In addition, wound matrix development and remodeling are enhanced by the increased collagen deposition and wound tensile strength mediated by nitric oxide. Fibroblast chemotaxis and migration are enhanced by nitric oxide activity, endothelial and epithelial cell proliferation and apoptosis regulation may also be correlated to wound nitric oxide activity. Boykin, J. V., *Nitric Oxide in Wound Healing*. See, also, Bauer J. A., Hydroxocobalamins as Biologically Compatible Donors of Nitric Oxide Implicated in the Acceleration of Wound Healing, Med Hypotheses, Jul. 1998 51:1, 65–7.

Nitric oxide regulation of hypertension is another promising direction. The cause of hypertension is not well-understood. At least one study suggests that hypertension can result from impaired endothelial NO activity, e.g., an inability to synthesize NO. Cardillo et al., Selective Defect in Nitric Oxide Synthesis May Explain the Impaired Endothelial-Dependent Vasodilation in Patients with Essential Hypertension, American Heart Association, Inc., 1998. Other studies with anti-oxidants such as Ginko Biloba and Ginsenosides have shown a direct relation with cerebral vasorelaxation, suggesting that increasing blood flow to the brain may be useful in treating ischaemia-induced cerebral dysfunction. See Chen et al., Extracts of Ginkgo Biloba and Ginsenosides Exert Cerebral Vasorelaxation via a Nitric Oxide Pathway, Clin. & Exp. Pharmacology and Physiology, v 24, 958–959 (1997). Of course, blood flow to the brain is most likely a contributing cause of hypertension. It is equally likely that an impaired endothelial NO activity in the kidneys, heart, etc., also contribute.

Unfortunately, known organic Nitric Oxide stimulants such as Ginseng and Ginkgo Biloba, taken orally, result in marginal increases in blood flow and are not viable treatment options for most conditions. They simply do not make up for the impaired endothelial NO activity. More powerful synthetic nitric oxide donors have been developed, but most have proven antagonistic to the immune system. Therefore, a significant demand exists for an effective nitric-oxide donor which is biologically friendly. Based on research, the present inventors have concluded that it would be greatly advantageous to combine the use of L-arginine with other natural and organic constituents as described above to stimulate enough release of NO to serve as a healing catalyst in both applications.

SUMMARY OF THE INVENTION

It is, therefore, an object of the present invention to provide a natural catalyst for the topical and/or oral treatment of wounds.

It is another object to combine the use of L-arginine with other natural and organic constituents to stimulate increased release of NO in the wound compartment to increase the speed and quality of healing.

It is another object to provide a natural relaxant for the treatment of hypertension. It is still another object to combine the use of L-arginine with other natural and organic constituents to stimulate increased release of NO to reduce hypertension.

According to the present invention, the above-described and other objects are accomplished by adapting the compound of L-arginine, ginseng and Zizyphi fructus as described in the '824 patent, and proving its efficacy in an orally or topically administered dosage for effective treatment for wound care and/or hypertension. In the wound-care context, the foregoing ingredients act synergistically to stimulate enough release of NO in the wound compartment. In the hypertension context, the ingredients act synergistically to stimulate enough release of NO to promote vasorelaxation, thereby increasing blood flow to the NO-synthesase impaired area and reducing hypertension.

The combination of ingredients, when administered in proper concentration, works to maintain a critical threshold level of NO in either the wound compartment or NO-synthesase impaired area in order to promote the healing process. The effect is sufficient to increase the speed and quality of systemic vascular relaxation and dilation, thereby promoting wound healing and/or reducing hypertension. The composition and topical and/or oral use thereof is entirely natural and harmless to the immune system.

BRIEF DESCRIPTION OF THE DRAWINGS

Other objects, features, and advantages of the present invention will become more apparent from the following detailed description of the preferred embodiment and certain modifications thereof when taken together with the accompanying drawings in which.

DETAILED DESCRIPTION OF THE PREFERRED EMBODIMENTS

Figure 1:
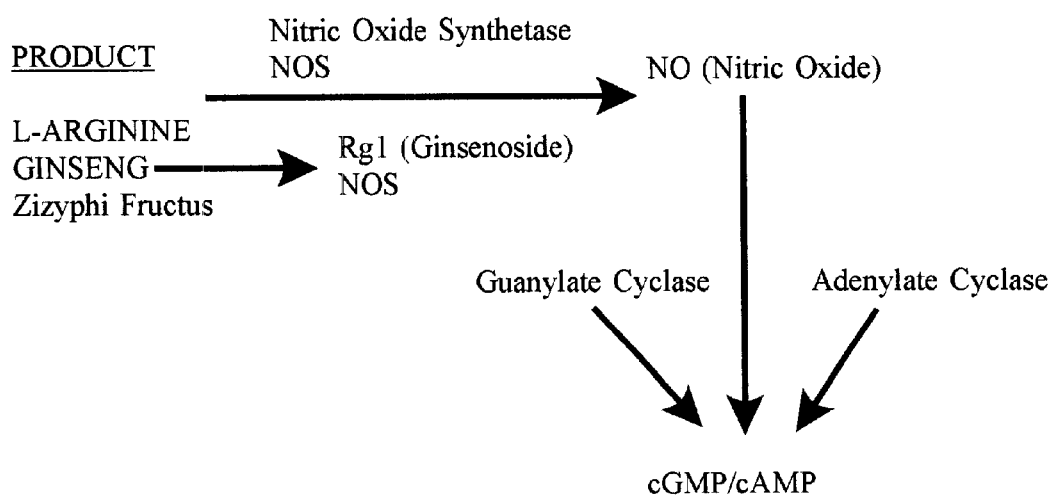
FIG. 1 is a flow diagram showing the mechanism by which the present invention stimulates increased levels of NO, thereby promoting systemic vascular relaxation and dilation.

As described above, past studies with natural ingredients have shown that a few have a tendency to increase synthesis of NO levels. These studies have had various purposes. For example, studies with natural medicines include ginseng, ginsenoside, and its purified derivative RG1. It has been shown that RG1 enhances the production of NO for killing certain tumor cells. See, e.g., Fan et al., Enhancement of Nitric Oxide Production from Activated Macrophages by a Purified Form of Ginsenoside (Rg1), American Journal of Chinese Medicine, Vol. XXHI, Nos. 3–4. pp. 279–287 (1995 Institute for Advanced Research in Asian Science and Medicine).

Another chinese anti-asthmatic herbal medicine, Zizyphi fructus (jujube), a derivative of Zizyphi Seeds, increases NO production. At least one study viewed the effects of Zizyphi fructus on NO generation on canines and found that Ziyphi fructus caused a concentration-dependent increase in NO. The results suggest that Ziyphi fructus enhances airway (tracheal) ciliary motility and that this effect is exerted through the stimulation of epithelial NO generation. See, Tamaoki et al., Ziyphi fructus, a Constituent of Antiasthmatic Herbal Medicine, Stimulates Airway Epithelial Ciliary Motility Through Nitric Oxide Generation, May–June; 22(3): 255–66, Exp Lung Res (1996).

The present inventors have found that the combination of Ziyphi fructus and ginseng (or its purified derivative ginsenoside or RG1) as described above, plus L-arginine, work synergistically to stimulate the release of NO in the corpus cavernosum. See, U.S. patent application Ser. No. 09/255,587 for "NATURAL COMPOSITION AND METHOD FOR THE TREATMENT OF SEXUAL DYSFUNCTION"; filed: Feb. 22, 1999.

In accordance with the present invention, each of the three constituents also has an individual tendency to enhance the release of NO in the wound compartment during the healing process. The combined constituents, when administered orally or topically in proper concentration, work to maintain a critical threshold level of NO in the wound compartment in order to promote the healing process. This synergistic effect increases the speed and quality of wound healing, yet the topical composition and use thereof is entirely natural and harmless to the immune system.

The inventor has found that the synergy stems from a catalyst effect: as illustrated in the flow diagram of FIG. 1 the Ziyphi fructus and ginseng speed up the conversion of L-arginine to NO. Thus, the combination of Ziyphi fructus, ginseng (or its purified derivative ginsenoside or RG1) as described above, plus L-arginine, when administered in proper concentration, stimulate sufficient release of NO in the wound compartment to catalyze the healing process. While any of the three constituents taken alone would be insufficient to produce the desired result, in combination they work synergistically to produce significant NO.

As seen in the flow diagram of FIG. 1, the additional NO is converted by guanylate cyclase, resulting in increased levels of cyclic guanosine monophosphate (cGMP) in the wound compartment. The cGMP in turn produces smooth muscle relaxation and improves arterial blood flow which results in improved healing of the wound compartment.

It should be understood that the proper relative concentrations of the three constituents may vary depending on the physical characteristics of each patient. However, preliminary research suggests that the desired effect is best achieved with a single dose comprising the following preferred concentrations and known acceptable ranges:

L-arginine: 200 mg (within a range of approximately 100–300 mg);

ginseng: 100 mg (within a range of approximately 50–200 mg); Ziyphi fructus: 7.2 micrograms per mililiter (within a range of +/−2.9 micrograms per mililiter).[1]

[1] The preferred concentrations of Ziyphi fructus is derived primarily from the Tamaoki et al. Article, supra.

The combined L-arginine, ginseng and Ziyphi fructus can be administered topically in ointment form, or orally in pill form. In either case it provides a safe, convenient and over-thecounter wound treatment remedy. The three constituents are purely organic, they have no known side-effects and have been time tested for other purposes. The product can be taken without a physician's prescription. Thus, sufferers of flesh wounds who choose not to seek medical help have a viable non-prescription alternative.

Of course, in addition to the above-described active ingredients, ancillary organic supplements such as Saw Palmetto, Ginkgo Biloba, L-Alanine, Glutamic Acid and L-Lysine may be added to increase the health benefits.

Moreover, further inert ingredients may be added as desired to achieve a desired taste, color or consistency.

In accordance with another embodiment of the present invention, each of the three constituents has an individual tendency to promote systemic vascular relaxation and dilation. The combined constituents, when administered orally in proper concentration, work to maintain a critical threshold level of NO in areas that are otherwise NO-synthesase-impaired, thereby reducing hypertension. The synergistic effect makes this the only known treatment for hypertension that is effective yet organic. Again, the synergy stems from a catalyst effect. As illustrated in the flow diagram of FIG. 1 the *Ziyphi fructus* and ginseng speed up the conversion of L-arginine to NO. Thus, the combination of *Ziyphi fructus*, ginseng (or its purified derivative ginsenoside or RG1) as described above, plus L-arginine, when administered in proper oral concentration, stimulate sufficient release of NO to promote systemic vascular relaxation and dilation in areas which otherwise are not capable of synthesizing NO, inclusive of the kidneys, heart and cerebrum. While any of the three constituents taken alone would be insufficient to reduce hypertension, in combination they work synergistically to produce enough NO and control the hypertension. As before, the additional NO is converted by guanylate cyclase, resulting in increased levels of cyclic guanosine monophosphate (cGMP). The cGMP in turn improves arterial blood flow in NO-impaired areas which in turn reduces hypertension.

Again, it should be remembered that the proper relative concentrations of the three constituents may vary depending on the physical characteristics of each patient. However, preliminary research suggests that the desired effect is best achieved with a single dose comprising the same above-described concentrations and ranges. The combined L-arginine, ginseng and *Ziyphi fructus* can be administered topically in ointment form, or orally in pill form. In either case it provides a safe, convenient and over-the-counter wound treatment remedy. The three constituents are purely organic, they have no known side-effects and have been time tested for other purposes. The product can be taken without a physician's prescription. Thus, sufferers of hypertension who choose not to seek medical help have a viable non-prescription alternative. Again, in addition to the above-described active ingredients, ancillary organic supplements such as Saw Palmetto, Ginkgo Biloba, L-Alanine, Glutamic Acid and L-Lysine may be added to increase the health benefits. Moreover, further inert ingredients may be added as desired to achieve a desired taste, color or consistency.

Having now fully set forth the preferred embodiment and certain modifications of the concept underlying the present invention, various other embodiments as well as certain variations and modifications of the embodiments herein shown and described will obviously occur to those skilled in the art upon becoming familiar with said underlying concept. It is to be understood, therefore, that the invention may be practiced otherwise than as specifically set forth in the appended claims.

We claim:

1. A composition for promoting circulation, comprising an effective amount of L-arginine, ginseng and *Ziyphi fructus*, said constituents being administered to stimulate release of NO in the body.

2. The composition for promoting circulation according to claim 1, wherein said constituents are administered periodically, each time in a single dose including a range of approximately 100–300 mg of said L-arginine, a range of approximately 50–200 mg of said ginseng, and a range of approximately 4.3–10.1 micrograms per milliliter of *Ziyphi fructus*.

3. The composition for promoting circulation according to claim 2, wherein said composition includes approximately 200 mg of said L-arginine, approximately 100 mg of said ginseng, and approximately 7.2 micrograms per milliliter of *Ziyphi fructus*.

4. The composition for promoting circulation according to claim 2, wherein said dose is in pill form for oral administration.

5. The composition for promoting circulation according to claim 2, wherein said dose is in liquid form for topical administration.

6. The composition for promoting circulation according to claim 1, further comprising saw Palmetto.

7. The composition for promoting circulation according to claim 1, further comprising Ginkgo Biloba.

8. The composition for promoting circulation according to claim 1, further comprising L-Alanine.

9. The composition for promoting circulation according to claim 1, further comprising Glutamic Acid.

10. The composition for promoting circulation according to claim 1, further comprising L-Lysine.

11. A composition for promoting healing of the human skin, comprising an effective amount of L-arginine, ginseng and *Ziyphi fructus*, said constituents being administered to stimulate release of NO in the skin.

12. The composition for promoting healing of the human skin according to claim 11, wherein said constituents are administered periodically, each time in a single dose including a range of approximately 100–300 mg of said L-arginine, a range of approximately 50–200 mg of said ginseng, and a range of approximately 4.3–10.1 micrograms per milliliter of *Ziyphi fructus*.

13. The composition for promoting healing of the human skin according to claim 12, wherein said composition includes approximately 200 mg of said L-arginine, approximately 100 mg of said ginseng, and approximately 7.2 micrograms per milliliter of *Ziyphi fructus*.

14. The composition for promoting healing of the human skin according to claim 12, wherein said dose is in pill form for oral administration.

15. The composition for promoting healing of the human skin according to claim 12, wherein said dose is in liquid form for topical administration.

16. A composition for reducing hypertension, comprising an effective amount of L-arginine, ginseng and *Ziyphi fructus*, said constituents being administered to stimulate release of NO in the skin.

17. The composition for reducing hypertension according to claim 16, wherein said constituents are administered periodically, each time in a single dose including a range of approximately 100–300 mg of said L-arginine, a range of approximately 50–200 mg of said ginseng, and a range of approximately 4.3–10.1 micrograms per milliliter of *Zizyphi fructus*.

18. The composition for reducing hypertension according to claim 17, wherein said composition includes approximately 200 mg of said L-arginine, approximately 100 mg of said ginseng, and approximately 7.2 micrograms per milliliter of *Ziyphi fructus*.

19. The composition for reducing hypertension according to claim 17, wherein said dose is in pill form for oral administration.

20. The composition for reducing hypertension according to claim 17, wherein said dose is in liquid form for topical administration.

* * * * *